(12) United States Patent
Ghai et al.

(10) Patent No.: US 7,247,488 B2
(45) Date of Patent: Jul. 24, 2007

(54) METHOD AND KIT FOR TESTING A MULTI-CHANNEL BLOOD ASSAY CARTRIDGE

(75) Inventors: Jyotsna Ghai, Plymouth, MN (US); Mark A. Thompson, Savage, MN (US); Colleen Lutz, Coon Rapids, MN (US); Narayanan Ramamurthy, Germantown, MD (US); Charlene X. Yuan, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 762 days.

(21) Appl. No.: 10/430,623

(22) Filed: May 6, 2003

(65) Prior Publication Data

US 2004/0224416 A1    Nov. 11, 2004

(51) Int. Cl.
*G01N 33/86* (2006.01)
(52) U.S. Cl. .............................. 436/69; 436/8; 436/63; 422/61; 422/73; 600/369; 73/64.41
(58) Field of Classification Search ................ 436/63, 436/69, 174, 8; 435/2; 422/61, 73; 600/369; 73/64.41
See application file for complete search history.

(56) References Cited

U.S. PATENT DOCUMENTS

| | | | |
|---|---|---|---|
| 4,731,330 A | 3/1988 | Hill et al. | |
| 4,795,703 A | 1/1989 | Folkman et al. | |
| 5,476,771 A * | 12/1995 | Reid et al. ..................... 435/13 |
| 5,526,111 A | 6/1996 | Collins et al. ................. 356/59 |
| 5,705,396 A | 1/1998 | Fickenscher et al. ......... 436/69 |
| 5,721,140 A | 2/1998 | Speck .......................... 436/16 |
| 5,906,942 A | 5/1999 | Speck .......................... 436/16 |
| 5,939,325 A | 8/1999 | Speck et al. .................. 436/16 |
| 5,951,951 A * | 9/1999 | Lane et al. .................... 422/73 |
| 5,972,712 A * | 10/1999 | Baugh et al. ................. 436/69 |
| 5,994,140 A | 11/1999 | Speck .......................... 436/16 |
| 6,010,911 A * | 1/2000 | Baugh et al. ................. 436/69 |
| 6,114,135 A | 9/2000 | Goldstein ..................... 435/13 |
| 6,124,110 A * | 9/2000 | Wober et al. ................. 435/13 |
| 6,194,394 B1 | 2/2001 | Hawkins ....................... 514/56 |
| 6,232,127 B1 * | 5/2001 | Lane et al. .................... 436/69 |
| 6,432,658 B1 | 8/2002 | Hoogendoorn et al. | |
| 6,541,262 B1 | 4/2003 | Baugh et al. | |
| 6,555,064 B2 * | 4/2003 | Baugh et al. ............... 422/68.1 |
| 6,555,381 B2 * | 4/2003 | Baugh et al. ................. 436/69 |
| 6,676,902 B2 * | 1/2004 | Baugh et al. ................. 422/73 |
| 2003/0113929 A1 | 6/2003 | Baugh | |

OTHER PUBLICATIONS

International Search Report from International Application No. PCT/US2004/014376 dated Sep. 1, 2004 (copy attached).
Website: www.analyticalcontrols.com/coagulat1.htm Analytical Control System, Inc.—Coagulation Controls and Platelet Depleted Plasma pp. 1-5, 2002.

(Continued)

*Primary Examiner*—Maureen M. Wallenhorst
(74) *Attorney, Agent, or Firm*—Mike Jaro; Jeffrey J. Hohenshell; Katharine A. Huebsch (57) ABSTRACT

A method and kit for testing a multi-channel blood-testing cartridge. In particular, blood-testing cartridges are tested with plasma samples with clotting times measured to indicate whether a batch of cartridges is suitable for testing the blood of a patient.

21 Claims, 5 Drawing Sheets

OTHER PUBLICATIONS

Website: www.analyticalcontrols.com/coagulat.htm Analytical Control Systems, Inc.—Coagulation Reagents, Calcium Chloride and Slides pp. 1-4, 2002.

Product description: RapidQC™ Bayer—Coagulation Controls for use the Rapidpoint Coag analyzer, date unknown.

Product insert: CLOTTrac CWB Coagulation / Citrated Whole Blood Coagulation Control and Non-Sterile Deionized Water for Reconstitution. 2 pages, Dec. 1999.

Product insert: CLOTTrac HR Abnormal Control / High Range Abnormal Control and Non-Sterile Deionized Water for Reconstitution. 2 pages, date unknown.

Database Biosis Online! Biosciences Information Service, Philadelphia, PA, US; 1980; Holmer et al. Properties of Antithrombin III Depleted Plasma I. Effect of Heparin: XP 002294515; Database accession No. PREV198069080209; abstract & Thrombosis Research Vo. 17, No. 102, 1980, pp. 113-124, ISSN: 0049-3848.

Pontius C A: "Finding control in quality control of unit-use prothrombin time test." MLO: Medical Laboratory Observer May 2001; Vo. 33 No. 5, May 2001 (2001-2005), pp. 38-40, 42, XP02294514; ISSN: 0580-7247.

* cited by examiner

METHOD AND KIT FOR TESTING A MULTI-CHANNEL BLOOD ASSAY CARTRIDGE

FIELD OF THE INVENTION

This invention relates to providing quality control for batches of multi-channel blood test cartridges by means of sampling and testing procedures.

BACKGROUND OF THE INVENTION

The management of hemostasis (control of bleeding) is an important requirement for a successful surgery. The exposure of blood to foreign surfaces, which often occurs during surgery, as well as the surgery itself, can induce the activation of the clotting factors.

The clotting mechanism can be mediated in a variety of ways. One of the more common methods of preventing coagulation is to administer heparin.

The administration of heparin, however, must be done carefully. Care is required because the response of any one patient to a particular dose of heparin is highly variable, depending upon the particular physiology of each patient. Thus, it is often quite necessary for physicians or other caregivers to understand the response of a patient such that a proper heparin dosage may be administered.

The Medtronic Hepcon® Hemostasis Management System Plus (HMS Plus) may be used to measure many blood parameters, including activated clotting time (ACT). The Medtronic Hepcon® HMS Plus system uses the ACT to base the Heparin Dose Response cartridge to measure individual response to heparin in vitro. The heparin dose response curve may be seen in FIG. 1.

The heparin dose response requires a small sample of whole blood from a patient. The whole blood is introduced into particular assay channels or vials, at least one (and preferably two) of the assay cartridge having no heparin reagent, at least one (and preferably two) more assay channels having a heparin reagent concentration of A and at least one (and preferably two) more assay channels having a heparin reagent concentration of B, where the concentration denoted as A is different from the concentration denoted as B.

Figure 1:
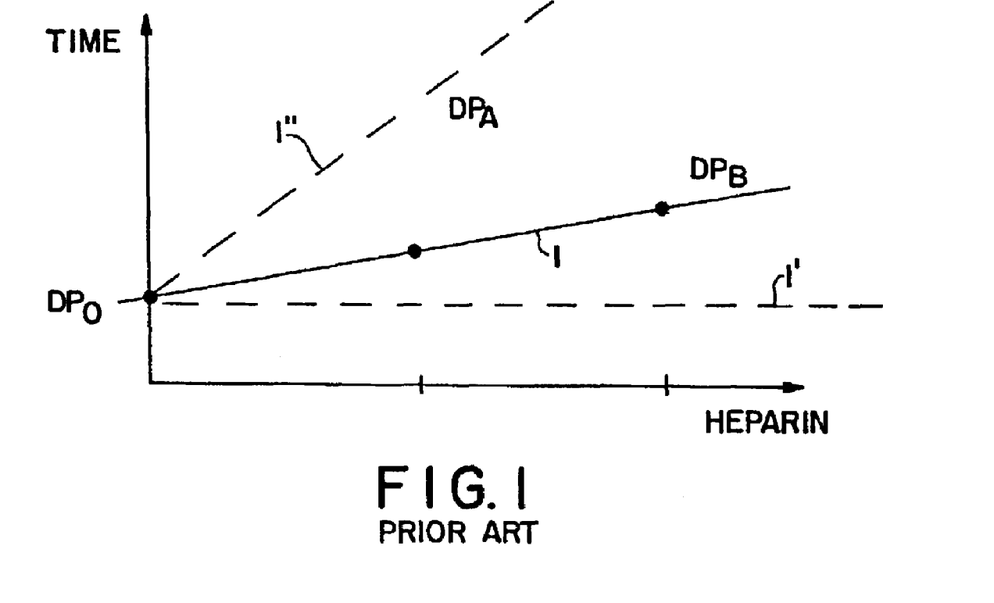
FIG. 1 is a graph for the clotting time of blood plotted against at least two levels of heparin, otherwise know as a heparin response curve according to the prior art.

The test begins by introducing the same volume of blood into each of the channels or vials. Thereafter the blood is mixed (preferably using a plunger.) The blood clots in each of the channels or vials at differing times. The clot is measured by timing the descent rate of the plunger. Ultimately, the clotting of each of the vials or channels may be graphed as shown in FIG. 1, where line 1 may be drawn through the three data points created by the time taken for blood to clot in each channel or vial. That is, blood without any heparin (depicted here as data point $DP_O$), blood with heparin reagent concentration A (depicted here as data point $DP_A$) and blood with heparin reagent concentration B (depicted here as data point $DP_B$). As seen, the heparin dose response is a linear function when the ACT is used to initiate coagulation.

The heparin dose response line varies from patient to patient. That is, the linear heparin dose response seen in FIG. 1 has different slopes for different individuals. Patients may have a heparin dose response line having slopes such as those seen as line 1' (very low slope) or line 1" (very high slope.) Generally speaking, the flatter or lower the slope of the line the more heparin resistant the patient is. Heparin resistant patients may have different reasons accounting for the heparin resistance. For example, these patients may have mechanisms which complex or bind the heparin, not allowing the heparin to inhibit blood coagulation. There may also be mechanisms present in the patient that rapidly eliminate the heparin. Finally, these patients may be heparin resistant due to low levels of the serine protease inhibitor antithrombin III (AT III). Heparin is a catalyst, that is, it helps prevent coagulation by accelerating the natural anticoagulant mechanisms present in the patient. The primary mechanism is the inhibition of thrombin, the primary protease of blood coagulation, by AT III. Without adequate amounts of AT III, heparin is ineffective in preventing blood coagulation.

AT III targets proteases of the coagulation cascade, and in particular thrombin. Heparin accelerates the rate with which AT III inhibits the proteases. Thus, without the presence of AT III, the anticoagulant activity of heparin is severely diminished. The differences in which individuals respond to heparin may be affected by the differences in their AT III levels. Thus, a goal of the present system is to provide a method of reliably assessing the heparin dose response while further accessing whether such heparin dose response is attributable to presence or absence of sufficient levels of AT III within the patient and whether the fresh whole blood (and thus patient) has, or requires additional, AT III.

Reference is made to a commonly owned U.S. Pat. No. 6,541,262 and corresponding PCT application WO 01/082793, which are incorporated by reference herein in their entirety. These references disclose a method for assessing the heparin dose response and whether the heparin dose response is attributable to the presence or absence of AT III.

A batch of test cartridges preloaded with reagents can be made in advance of testing a blood sample by means of an HMS Plus-type machine and may be stockpiled at a medical or surgical facility for convenient use during a medical or surgical procedure. Test cartridges are then taken from the stored batch of cartridges, as they may be needed for testing while other test cartridges remain in storage. However, a practical difficulty with stored reagents in the test cartridges is to have assurance that the stored reagents will remain active and will produce consistent, reliable results as the cartridges in the batch age.

SUMMARY OF THE INVENTION

The present invention provides a method for quality testing of test cartridges. The test cartridges are designed to test a sample of fresh whole blood in test cartridges having preloaded reagents that can be stored and used after storage with assurance that the test cartridges will provide accurate results. In particular, the present invention employs quality control samples that when tested in stored cartridges selected from a batch of stored cartridges can assure that the entire batch of stored cartridges will provide accurate results as they are subsequently drawn from the batch and used. By withdrawing cartridges from the batch on a predetermined schedule and testing them with the quality control sample, a determination can be made that the entire batch of stored cartridges is still good. That is, that a cartridge that is subsequently withdrawn from the batch and used before the next scheduled test (time) with a sample of fresh whole blood will give an accurate determination as to the condition of the patient's blood. In a preferred embodiment the blood factor used in the test cartridge is the serine protease inhibitor Antithrombin III (AT III). The preferred cartridge provides for testing of a whole blood sample within at least three testing channels in duplicate, a first set of channels, a second set of channels and a third set of channels all provided within an integral cartridge. The first channel contains a portion of the single whole blood sample along with an anticoagulant/antithrombotic agent in the reaction chamber. The second channel contains a portion of a single whole blood sample along with the anticoagulant/antithrombotic agent and a blood factor that is involved in controlling the coagulation cascade in the reaction chamber. The third channel is a control channel and contains a portion of a single whole blood sample without any additives in the reaction chamber. In a preferred embodiment, the anticoagulant/antithrombotic agent may be selected from glycosaminoglycans which have the anticoagulant sequence which binds to the blood factor which is involved in controlling the coagulation cascade. In the preferred embodiment the anticoagulant/antithrombotic agent is heparin and the blood factor that is involved in controlling the coagulation cascade is AT III. Each channel is provided with a device for assessing when a clot is formed. The time for the formation of a clot in each channel may be used to determine whether the patient would have a modified heparin response from the administration of a blood factor prior to surgery. In a preferred embodiment the method may be performed within the Medtronic Hepcon® Hemostasis Management System Plus (HMS Plus). The present invention may be practiced with a test cartridge used within the Medtronic Hepcon® HMS Plus containing the appropriate reagents, identified above, in the testing cartridges.

The quality control samples used in the invention include a plasma sample that is deficient in the blood factor reagent to be tested. For example, when testing for AT III as a cartridge blood factor reagent, at least one plasma sample is an AT III-deficient plasma but otherwise has substantially the same clotting ability as a normal plasma sample. The quality control samples used in the invention also include a plasma sample that includes an agent that is capable of neutralizing the anticoagulant/antithrombotic reagent. For example, when testing for a heparin reagent, a sample can be a plasma sample with a heparin-neutralizing agent but otherwise has substantially the same clotting ability as a normal plasma sample. Preferably at least two plasma samples are used. For example, one can use the plasma with an anticoagulant/antithrombotic neutralizer in a first test cartridge followed by blood factor deficient plasma in a second test cartridge. The clotting time result for the two plasmas can then be examined and compared to determine whether the batch or lot of cartridges is still good. A clotting time range is established during manufacturing for each batch or lot of the blood factor deficient plasma for each of the three set of channels provided within an integral cartridge. Similarly, a clotting time range is established during manufacturing for each batch or lot of the plasma with an anticoagulant/antithrombotic neutralizer for each of the three channels provided within an integral cartridge. If the clotting times fall within the clotting time range, then the batch or lot of cartridges is still good.

If the cartridges to be tested do not include a blood factor as a reagent, but instead include only an anticoagulant/antithrombotic as a reagent, the quality control samples of the invention can also be used. The quality control samples include a plasma sample that includes an agent capable of neutralizing the anticoagulant/antithrombotic reagent. For example, this can be a plasma sample with a heparin-neutralizing agent. The quality control samples also include a plasma sample that will respond to the presence of the anticoagulant/antithrombotic agent. For example, AT III-deficient plasma sample could be used. A normal plasma sample could also be used to monitor anticoagulant effect if thromboplastin is used as activator.

Preferably, the plasma samples are provided in a form that allows them to be stored for extended periods of time, such as lyophilized plasma samples or plasma samples containing stabilizers. Also preferably, the plasma samples should include any diluents or reagents that may be needed to constitute a correct concentration or composition to be tested in the test cartridge or such diluents and reagents may be supplied separately from the plasma samples or together with the plasma samples as a kit.

The test procedure according to the invention is to withdraw from a batch of stored cartridges at least the same number of cartridges as the number of quality control plasma samples to be tested. At least two cartridges are to be used in order to test for proper assessment of the heparin dose response and/or whether the heparin dose response is attributable to the presence or absence of AT III. The plasma test samples are introduced into the test cartridge in substantially the same manner as a sample of fresh, whole blood is introduced into the cartridge according to the instructions for use and the cartridge is inserted into the test apparatus such as the Hepcon® HMS Plus. The apparatus provides clotting times for each channel of the test cartridge. Clotting times for all channels of the cartridge should be roughly the same for the neutralized-heparin sample, since each channel should clot equally well with the heparin neutralized in each channel. In the channel of the cartridge containing both heparin and AT III as reagents, the AT III-deficient plasma should not clot. A clotting time range is set during manufacturing for each batch or lot of the AT III-deficient plasma for each of the three channels within the cartridge. Similarly, a clotting time range is set during the manufacturing for each batch or lot of the plasma with a heparin neutralizer for all three channels within the cartridge. If the clotting times fall within the clotting time range, then the batch or lot of cartridges is still good.

With respect to cartridges that depart from these expected results, the batch or lot of cartridges should be discarded.

DETAILED DESCRIPTION OF THE FIGURES

FIG. 1 is a graph for the clotting time of blood plotted against at least two levels of heparin, otherwise know as a heparin dose response curve according to the prior art. As discussed above, such a graph may be created through the Medtronic Hepcon® Heparin Dose Response (HDR) assay performed in the Medtronic Hepcon® Hemostasis Management System Plus (HMS Plus) automated testing device. As known, such a test is used to test the response of a fresh, whole blood sample to a variety of heparin doses. As seen, at least three data points are collected, depicted here as DP-0, DP-A and DP-B.

In the current Hepcon® HMS Plus, three data channels are used in duplicate, while as little as two sets are needed to ascertain the linear heparin dose response. The excess channel capacity can be used to concurrently create data of a heparin response with an additional amount of a blood factor such, as AT III, which is involved with the coagulation cascade. Through such a system, data may be concurrently collected to both determine the heparin dose response, as well as the effect on such response to the addition of an added blood factor which is involved with the coagulation cascade. A graph that may be created with the use of the added blood factor is shown in FIG. 2.

Figure 2:
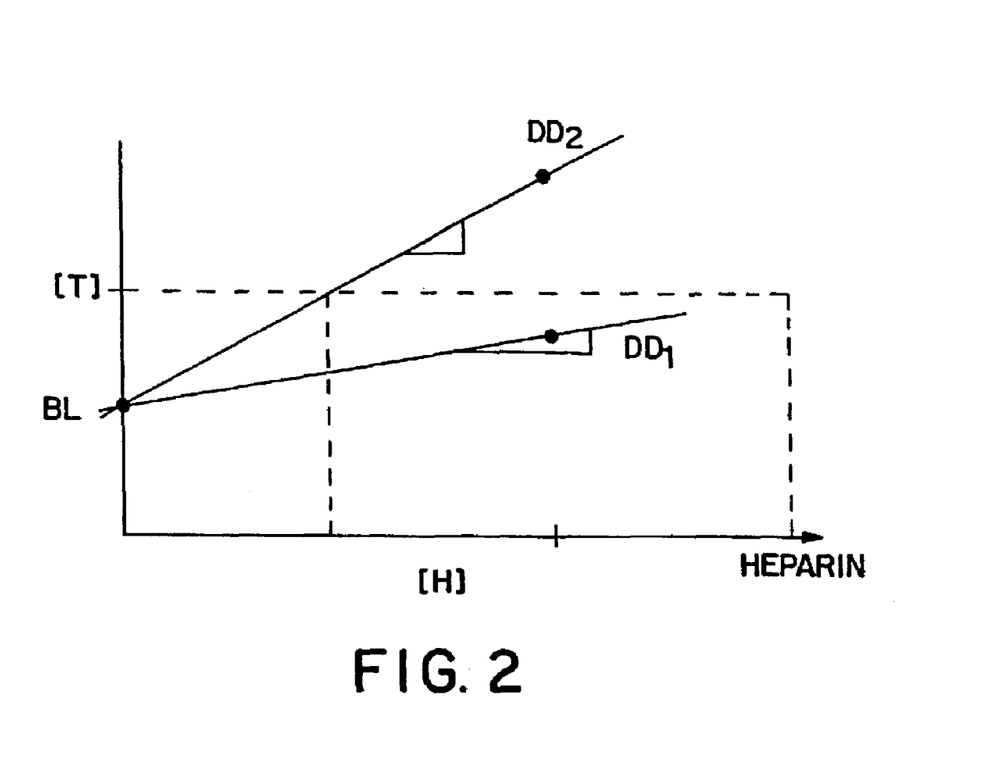
FIG. 2 is a graph for the clotting time of a sample of blood in which the heparin dose response is determined while the blood is provided with at least one level of a reagent that affect the anticoagulant activity of heparin.

FIG. 2 is a graph for the clotting time of a sample of blood in which the heparin dose response is determined while the blood is provided with at least one level of a reagent that affects the anticoagulant activity of heparin with a known amount of heparin. As seen, BL represents a baseline data point depicting the time required for a sample of fresh whole blood to clot in a specified channel or vial. Specific details of the channel or vial are described below. DD-1 represents a data point depicting the time required for a sample of fresh whole blood to clot in a specified channel or vial in the presence of a specified amount of heparin. DD-2 represents a data point depicting the time required for a sample of fresh whole blood to clot in a specified channel or vial in the presence of a specified amount of heparin and also in the presence of a blood factor that is involved with the coagulation cascade. In the preferred embodiment, this blood factor is AT III. While in this depiction the data point DD-2 is shown as being above DD-1, the specific relationship between these data points will vary from patient to patient.

Figure 3:
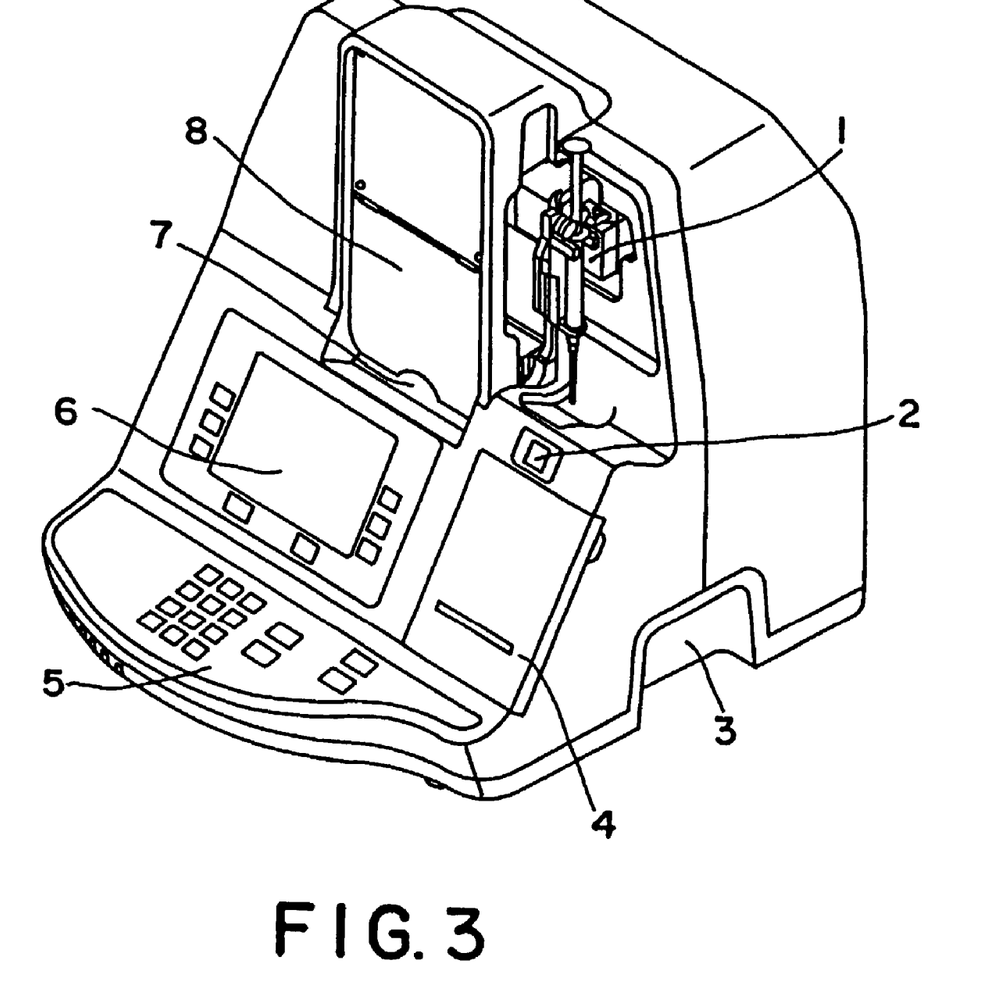
FIG. 3 is a perspective view of the Hepcon® HMS Plus instrument within which a test or assay cartridge may be used.

FIG. 3 is a perspective view of the Hepcon® HMS Plus instrument within which a test or assay cartridge may be used. The Hepcon® HMS Plus is a microprocessor based, multi-channel clot timing instrument with automated syringe handling for pipetting blood into single use cartridges. It performs in vitro blood evaluations including heparin sensitivity evaluations, heparin assays, activated clotting times, and platelet function evaluations. As seen the Hepcon® HMS Plus instrument includes a sample dispenser/syringe 1, a start/stop key 2, a carry handle 3, a printer 4, main keypad 5, LCD screen and keys 6, heat block and cartridge receiver 7, and a protective shield 8. The Hepcon® HMS Plus instrument is available from Medtronic Inc., Minneapolis, Minn.

Figure 4:
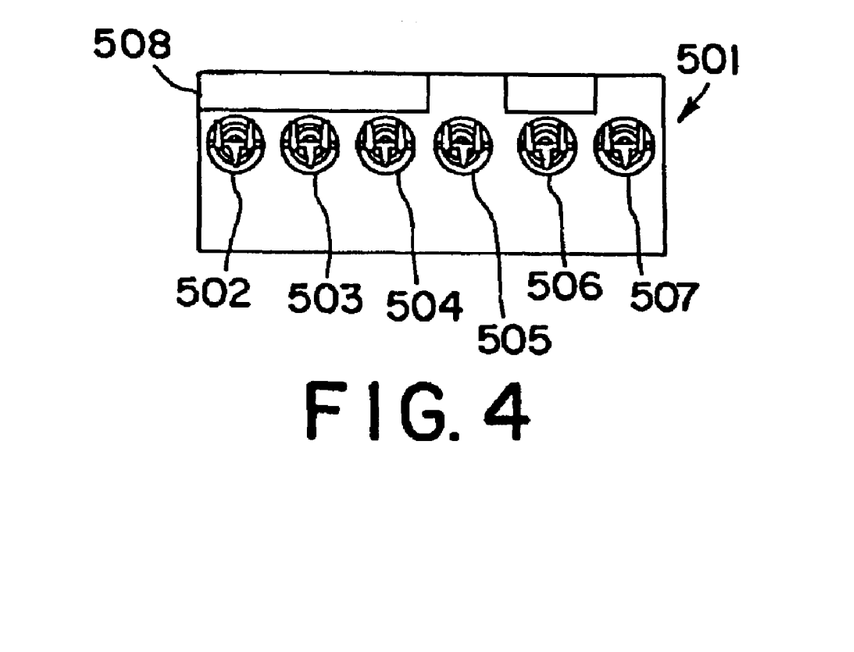
FIG. 4 is a top plan view of a test or assay cartridge 501 used with the instrument shown in FIG. 3.

FIG. 4 is a top plan view of a test or assay cartridge 501 used with the instrument shown in FIG. 3 within which the present invention may be used. As seen the cartridge 501 includes a plurality of channels 502–507. Positioned upon the top of housing is an optical code 508. The purpose of the optical codes is to let the Hepcon® HMS Plus instrument detect (via the software) what type of assay is being performed. Since there are a number of different assays that may be performed on the instrument, it is required which type of assay is to be performed so that the clotting data can be analyzed correctly. Of course a variety of other schemes could be used, as opposed to optical codes, such as user-input, magnetic, EEPROM, reflective or bar code.

Figure 5:
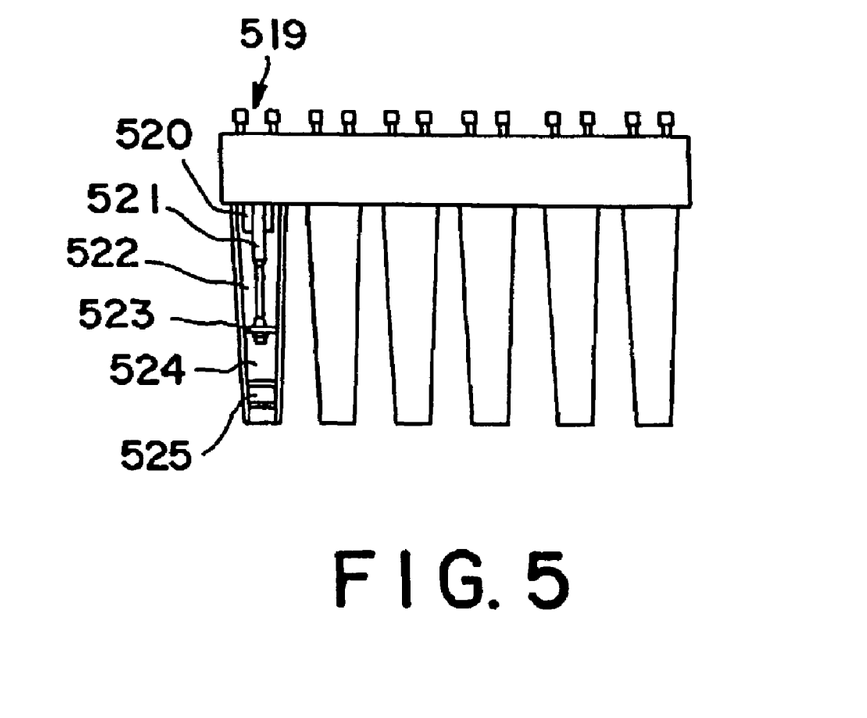
FIG. 5 is a side plan view of the cartridge 501 shown in FIG. 4.

FIG. 5 is a side plan view of the cartridge 501 shown in FIG. 4. As seen, each channel 502 contains a plunger 519. Plunger 519, extends above the upper surface of housing so as to be able to be actuated, upwardly and downwardly, by a testing device, such as the Hepcon® HMS Plus, discussed above. As further seen plunger 519, features plunger flag 520 along the upper portion. Plunger shaft 521 continues downwardly to daisy plug 523. Defined between daisy plug 523 and bottom plug 525 is reagent chamber 524. Thus, daisy plug 523 defines above it an upper reaction chamber 522, within which fresh whole blood is added, while daisy plug 523 defines below it the reagent chamber 524. As can be appreciated, movement of the plunger, and then the plunger daisy, upward removes the daisy plug from its position as shown and allows fluids within the reaction chamber 522 and reagent chamber 524 to mix.

As discussed above, the test employing the blood factor can be carried out using a cartridge having a series of at least three separate channels. In the preferred embodiment, each channel is repeated at least once so that three channels, each repeated once, therefore six channels may be used. Each channel is constructed the same as that described above, although the compounds within the reaction and reagent chambers for each channel may vary (Further details may be found in U.S. Pat. No. 5,951,951, incorporated herein by reference).

In a preferred embodiment, in the first channel, the reagent chamber features a solution to promote contact activated coagulation (intrinsic coagulation cascade). The reaction chamber further has positioned within a primary reagent, such as a primary reagent to inhibit blood coagulation, preferably heparin. Preferably the heparin is provided in the amount of between approximately 0.1–10.0 Units per milliliter (Units/ml), and preferably in the amount to give a sample concentration of approximately 2.5 Units/ml. In the preferred embodiment, this heparin is provided in a dried form, (may be used wet or in any other formation), dried to the inner surface of the reaction chamber such that it is dissolved upon contact with the fresh whole blood sample.

In the second channel, the reagent chamber features a solution to promote contact activated coagulation (intrinsic coagulation cascade). The reaction chamber of the second channel further has positioned within a primary reagent, such as a primary reagent to inhibit blood coagulation, preferably heparin. Preferably the heparin is provided in the amount of between approximately 0.1–10.0 Units/ml, and preferably in the amount to give a sample concentration of approximately 2.5 Units/ml. In the preferred embodiment, this heparin is provided in a dried form, dried to the inner surface of the chamber such that it is dissolved upon contact with the fresh whole blood sample. The second channel further features a blood factor which is involved with the coagulation cascade, and preferably a blood factor which targets proteases of the coagulation cascade, and in particular thrombin. In the preferred embodiment, this blood factor is AT III provided in the amount to give a sample concentration of between approximately 0.1–10.0 Units/ml, and preferably in the amount of approximately 0.8 Units/ml (80 U/dL). In the preferred embodiment, this AT III is also provided in a dried form, dried to the inner surface of the reaction chamber such that it is dissolved upon contact with the fresh whole blood sample. A stabilizer such as BSA is also used to stabilize ATIII to extend the shelf life of the reagent.

TABLE ONE

| Channel | Reagent chamber | Reaction chamber |
| --- | --- | --- |
| First channel | 12% kaolin in a buffered isotonic saline solution | 2.5 Units/ml Heparin |
| Second channel | 12% kaolin in a buffered isotonic saline solution | 2.5 Units/ml Heparin Physiological concentration of ATIII(0.8–1.2 Units/ml ATIII) |
| Third channel | | Blank |

The third channel chamber does not have, within the reaction chamber, any reagents. In the third channel reagent chamber, however, a suspension/solution is provided to promote contact activated coagulation (intrinsic coagulation cascade). Like the same solution in the first and second channel, this is provided so as to accelerate coagulation because without such a compound the time required for a clot to form would be extensive In use, it is important to note the order in which the channels are filled with sampled blood. Channels that contain anticoagulant are pipetted first and those that do not contain anticoagulant are filled last. This order or sequence prevents some premature activation of the baseline sample in the cartridge. That is, otherwise the cartridge body would activate blood while the other channels were being filled. Even though the total time required for such fill is small, the effect on the blood and the test results is to be avoided.

Figure 6:
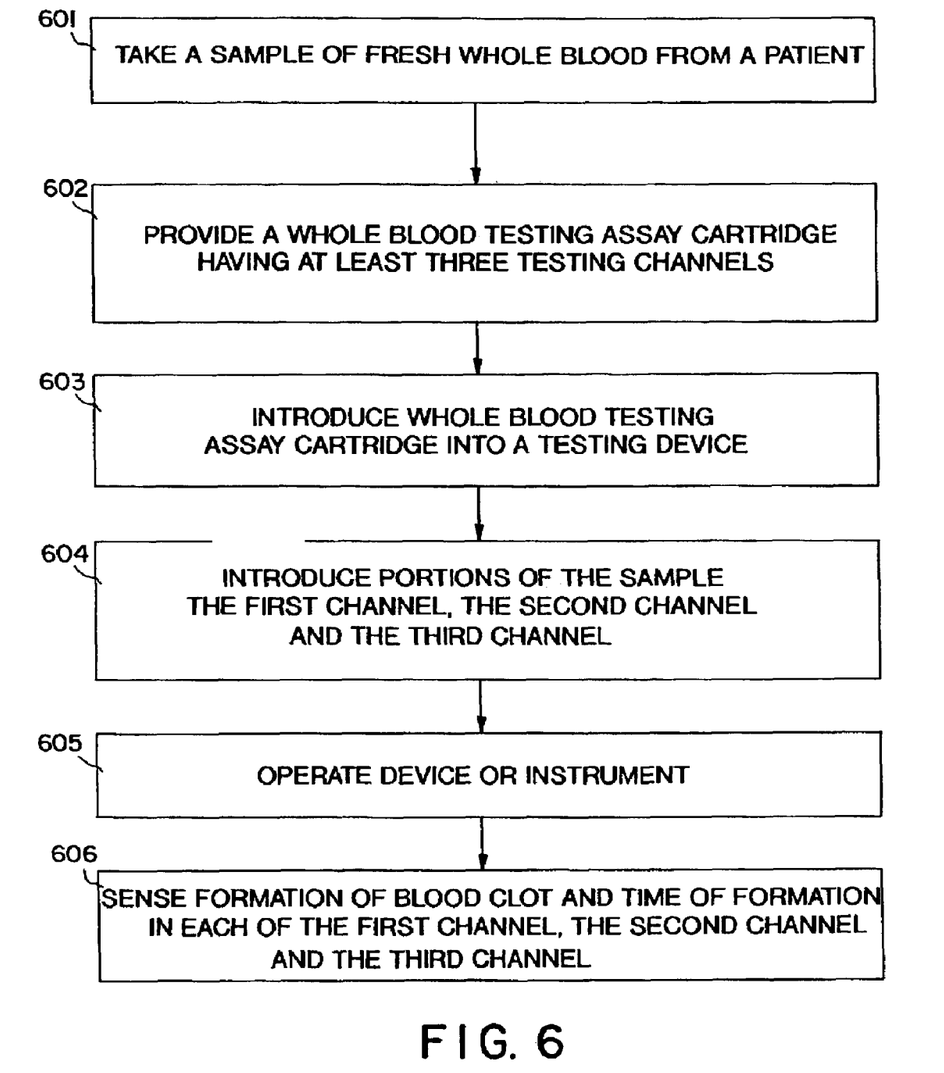
FIG. 6 depicts a method of determining whether a patient would have a modified heparin response from the administration of a blood factor.

The test performed with the test cartridges can be used for determining whether a patient's heparin response would be modified by the administration of a blood factor. Such a method is depicted in FIG. 6. At 601 a sample of fresh whole blood is taken from a patient. At 602 a whole blood testing assay cartridge is provided, the cartridge having at least three testing channel. The cartridge is preferably constructed as described above with regards to FIG. 4. At 603, the cartridge is placed into the instrument. At 604, the instrument automatically introduces the sample into the assay cartridge. At 605 the instrument actuates the cartridge and begins testing for clot formation in the cartridge channels. The device operates to both mix the blood in each channel, preferably through the upward and downward movement of the plunger, as well as to sense the formation and presence of a blood clot. Next, at 606, the formation of a blood clot and its time of detection are sensed and noted for each of the first channel, second channel and the third channel. The times for each clot formation in each channel may thereafter be used to determine whether a patient's response to an anticoagulant/antithrombotic would be modified by the administration of a blood factor prior to surgery. It should be noted, incidentally, that the instrument does not actually supply a plot of the resulting information, but rather computes the slope of the responses. The graph essentially illustrates what the instrument is doing via mathematical calculations. The instrument makes the comparison of the slopes, and if the slope increases by more than an amount determined through reference range testing, the instrument gives an indication that the addition of AT III will modify the patient's response to heparin.

The quality control samples used in the invention include plasma samples. If the cartridge to be tested includes a blood factor as a reagent, at least one of the plasma samples must be deficient in the blood factor reagent to be tested. The quality control samples used in the invention also include at least one plasma sample in which the anticoagulant/antithrombotic agent has been neutralized. For example, when testing for a heparin reagent, a sample can be plasma with a heparin neutralizer but otherwise has substantially the same clotting ability as a normal plasma sample. For example, a preferred method for making plasma with a heparin neutralizer is to use a normal plasma together with a heparin neutralizer of hexadimethrine bromide (Polybrene®) in an amount in a concentration of about 0.1 to 10.0 micrograms/milliliter, and preferably in an amount to give a sample concentration of at least about 1.0 micrograms/milliliter. Other polycationic quartenaryamine, such as polylysine or polyargnine heparinase, and/or protamine in an amount that will neutralize the heparin in the test cartridge could also be used. When testing for AT III as a reagent, a sample can be an AT III-deficient plasma but otherwise contains substantially the same clotting ability in the absence of heparin as a normal plasma sample. Preferably, the plasma samples are provided in a form that allows them to be stored for extended periods of time, such as lyophilized plasma samples or plasma samples containing stabilizers. A preferred normal plasma is lyophilized, citrated sheep plasma that has been stabilized with a citrate in a concentration of about 0.1 to 10.0% and preferably about 3.8%. A preferred AT III-deficient plasma is lyophilized, citrated AT III-deficient human plasma in a HEPES buffer in a concentration of about 1.0 to 100 mM and preferably in the concentration of 20 mM. Also preferably, the plasma samples used in the test should include any diluents or reagents that may be needed to constitute a correct concentration or composition to be tested in the test cartridge or such diluents and reagents may be supplied separately from the plasma samples or together with the plasma samples as a kit. For example, a kit can include a sample of lyophilized plasma in one vial and a diluent for the lyophilized plasma in another vial that can reconstitute the plasma. The sample of lyophilized plasma could represent about 2.5 ml of plasma before lyophilization and the diluent should be supplied in the correct amount needed to reconstitute the plasma (i.e. about 2.5 ml of diluent). The first vial could be large enough to conveniently mix the correct amount of the diluent with the lyophilized plasma (i.e. about 6 ml). The volume of the vial in the kit containing the diluent should also be at a convenient size (i.e. about 6 ml). The kit can contain a number of plasma vials and corresponding diluent vials. For example, a kit could include 10 vials of lyophilized AT III-deficient plasma and 10 vials of diluent so that any vial of diluent could be used to reconstitute any vial of the plasma. A preferred kit including normal sheep plasma would include lyophilized sheep plasma in a first vial and the correct amount of deionized water and heparin neutralizer in a second vial. A kit could include multiple vials such as 10 vials of sheep plasma with 10 vials containing a diluent and a heparin neutralizer such that any of the vials containing diluent and heparin neutralizer could be used to reconstitute any of the vials of plasma and the reconstituted plasma could neutralize heparin in the cartridge. Of course, all of the vials would be provided with adequate seals to protect the contents during shipment and storage.

The preferred AT III-deficient plasma is citrated human plasma that has been depleted of AT III by heparin affinity chromatography and/or by using antibodies directed to antithrombin immobilized on agarose beads. This is commercially made from normal citrated human plasma and is available from Affinity Biologicals. In general, plasmas suitable for use in the invention can be from either human or animal sources. Other suitable ways for making plasmas in which AT III is deficient include: (1) the use of excess thrombin; (2) the use of other AT III binding proteins such as Xa (3) the use of other competitive inhibitors and/or co-factors of AT III.

Other reagent substitutions are possible for use in the invention include (1) the use of direct thrombin inhibitors such as hirudin or Argatroban® in place of AT III (2) a polysaccharide in place of heparin (3) thromboplastin, glass beads, and/or celite (diatomaceous earth) in place of Kaolin.

Figure 7:
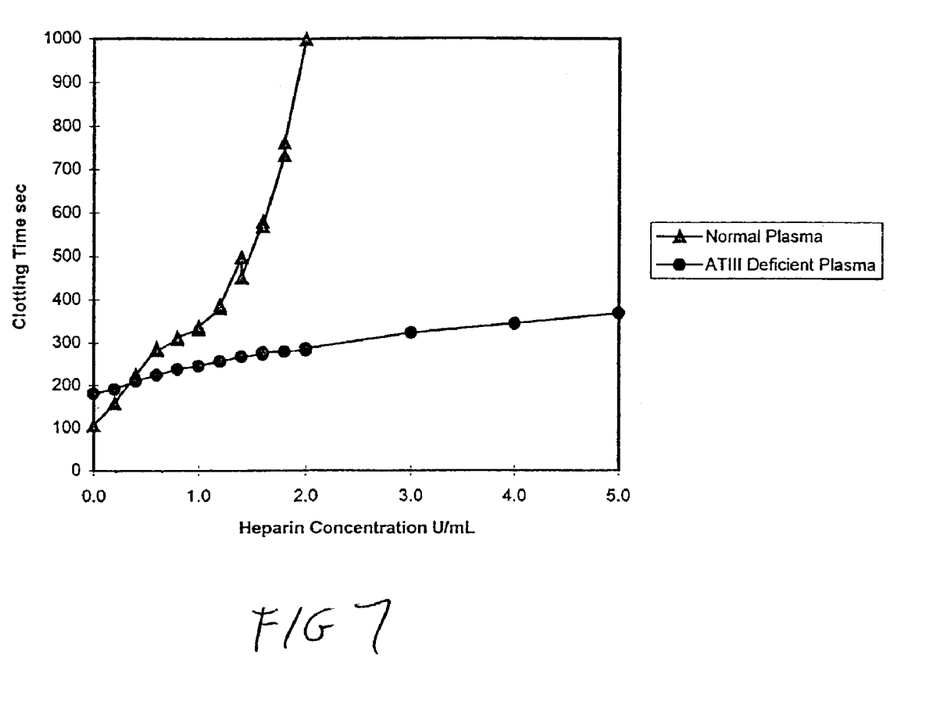
FIG. 7 is a graph of clotting time comparing AT III-deficient plasma with normal plasma.
Figure 8:
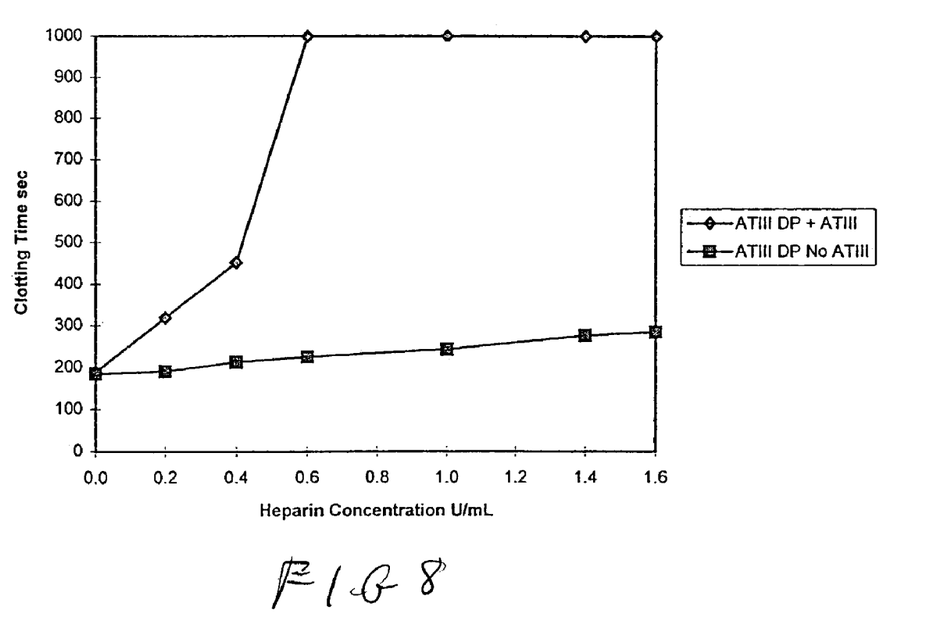
FIG. 8 is a graph of clotting time for AT III-deficient plasma comparing cartridge channels with and without AT III The FIGS are not necessarily to scale.

FIG. 7 depicts the results from a test of AT III-deficient plasma in comparison with normal plasma. Heparin strongly influences clotting time for the normal plasma while heparin is shown to have only a modest effect on clotting time for AT III-deficient plasma. FIG. 8 depicts the results from a test in which AT III is added back into test samples of AT III-deficient plasma. The effect of heparin on clotting time is restored by the presence of additional AT III.

EXAMPLE 1

Test cartridges were built with heparin and AT III as reagents. Each channel of each cartridge was filled at the bottom with 88 µl of kaolin. The top of each of the cartridges were filled with solutions containing heparin alone or heparin with AT III according to the following table:

| Channel Number | Reagents | AT III(Units/ml) | Heparin (Units/ml) |
|---|---|---|---|
| 1 | Heparin | — | 2.5 |
| 2 | Heparin | — | 2.5 |
| 3 | Heparin + AT III | 0.8 | 2.5 |
| 4 | Heparin + AT III | 0.8 | 2.5 |
| 5 | — | — | — |
| 6 | — | — | — |

Cartridges were then tested in a Hepcon® HMS Plus instrument using normal pooled plasma as a test sample with the following coagulation time results:

| Channel | AT III (Units/ml) | Heparin (units/ml) | Cartridge 1 (seconds) | Cartridge 2 (seconds) | Cartridge 3 (seconds) | Cartridge 4 (seconds) | Cartridge 5 (seconds) |
|---|---|---|---|---|---|---|---|
| 1 | 0 | 2.5 | >999 | >999 | >999 | >999 | >999 |
| 2 | 0 | 2.5 | >999 | >999 | >999 | >999 | >999 |
| 3 | 0.8 | 2.5 | >999 | >999 | >999 | >999 | >999 |
| 4 | 0.8 | 2.5 | >999 | >999 | >999 | >999 | >999 |
| 5 | 0 | 0 | 108 | 108 | 108 | 109 | 113 |
| 6 | 0 | 0 | 110 | 108 | 108 | 109 | 113 |

EXAMPLE 2

Cartridges from Example 1 were then tested in a Hepcon® HMS Plus instrument using AT III-deficient plasma as a test sample with the following coagulation time results:

| Channel | AT III (Units/ml) | Heparin (Units/ml) | Cartridge 1 (seconds) | Cartridge 2 (seconds) | Cartridge 3 (seconds) | Cartridge 4 (seconds) | Cartridge 5 (seconds) |
|---|---|---|---|---|---|---|---|
| 1 | 0 | 2.5 | 322 | 322 | 328 | 321 | 336 |
| 2 | 0 | 2.5 | 322 | 322 | 328 | 328 | 343 |
| 3 | 0.8 | 2.5 | >999 | >999 | >999 | >999 | >999 |
| 4 | 0.8 | 2.5 | >999 | >999 | >999 | >999 | >999 |
| 5 | 0 | 0 | 177 | 177 | 180 | 180 | 188 |
| 6 | 0 | 0 | 177 | 177 | 180 | 180 | 188 |

A comparison of the results of testing the cartridges with normal pooled plasma confirms the normal activity of both the heparin and the AT III in the test cartridges.

EXAMPLE 3

Test cartridges were prepared as in example 1. Plasma samples were prepared from pooled human plasma. Each of the 2.5 ml lyophilized plasma samples were reconstituted with a solution of deionized water and hexadimethrine bromide (Polybrene®) to form heparin-deficient plasma samples. The Polybrene® solution was prepared from a stock solution prepared with 0.9% saline solution and sufficient Polybrene® to provide a concentration of 10 mg/ml. The stock solution was then diluted with deionized water in the amount of 20 µl of stock solution to 1.8 ml of water for each plasma sample. Three cartridges were then tested in a Hepcon® HMS Plus™ instrument using 200 µl of the heparin-deficient plasma in each cartridge channel as a test sample at 0 minute, 30 minute and 60 minute incubation times with the following coagulation time results:

| Channel | AT III (Units/ml) | Heparin (Units/ml) | 0 Minutes (seconds) | 30 Minutes (seconds) | 60 Minutes (seconds) |
|---|---|---|---|---|---|
| 1 | 0 | 2.5 | 147 | 162 | 186 |
| 2 | 0 | 2.5 | 144 | 165 | 168 |
| 3 | 0.8 | 2.5 | 136 | 162 | 172 |
| 4 | 0.8 | 2.5 | 141 | 178 | 179 |
| 5 | 0 | 0 | 141 | 162 | 165 |
| 6 | 0 | 0 | 136 | 159 | 168 |

The relative uniformity of these test results from channel to channel and at different incubation times is indicative of properly functioning cartridges. Additional tests have shown that the test is also insensitive to the volume of plasma used as the quality control samples since samples having more or less Polybrene® provide substantially the same result.

EXAMPLE 4

A 'new' range is calculated for each batch of controls during manufacturing. The following approximate ranges were determined by taking the average ±3 SD for several cartridges.

QC Level 1 HDR & HDR/ATIII (2 Lots, 10 Cartridges Each)
Channels 1–6 102–141 seconds QC Level 2 HDR (1 Lot, 9 Cartridges):
Channels 1&2 254–314 seconds
Channels 3&4 224–250 seconds
Channels 5&6 183–203 seconds QC Level 2 HDR/ATIII (2 Lots, 10 Cartridges)
Channels 1&2 250–340 seconds
Channels 3&4 >600 seconds (no clot will form)
Channels 5&6 177–211 seconds Although a specific embodiment of the invention has been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components that perform substantially the same function in substantially the same way to achieve substantially the same result for those described herein.

What is claimed is:

1. A method comprising the steps of:
selecting a first test cartridge having a first channel with an anticoagulant/antithrombotic as a reagent therein and a second channel without the anticoagulant/antithrombotic as a reagent therein;
preparing a first plasma sample that has a clotting time that may be altered by the presence of the anticoagulant/antithrombotic reagent;
adding a first portion of the first plasma sample to the first channel of the first cartridge; adding a second portion of the first plasma sample to the second channel of the first cartridge;
determining the time required for a clot to be formed in each of the first and second channels for the first plasma sample;
preparing a second plasma sample that includes an agent capable of neutralizing the anticoagulant/antithrombotic reagent;
selecting a second test cartridge having a first channel with the anticoagulant/antithrombotic as a reagent therein and a second channel without an anticoagulant/antithrombotic as a reagent therein;
adding a first portion of the second plasma sample to the first channel;
adding a second portion of the second plasma sample to the second channel; and
determining the time required for a clot to be formed in each of the first and second channels for the second plasma sample, wherein the anticoagulant/antithrombotic reagent is heparin.

2. The method according to claim 1, wherein the first channel of the first cartridge and the first channel of the second cartridge has heparin as a reagent in the amount of between approximately 0.1–10.0 Units/ml.

3. The method of claim 1, wherein the second plasma sample includes protamine as the neutralizing agent.

4. The method of claim 1, wherein the second plasma sample includes a polycation as the neutralizing agent.

5. The method of claim 1, wherein the second plasma sample includes a quartenaryamine as the neutralizing agent.

6. The method of claim 1, wherein the second plasma sample includes hexadimethrine bromide as the neutralizing agent.

7. The method of claim 1, wherein the second plasma sample includes heparinase as the neutralizing agent.

8. A method comprising the steps of:
selecting a first test cartridge having a first channel with a anticoagulant/antithrombotic as a reagent therein;
a second channel with the anticoagulant/antithrombotic as a reagent therein and also with a blood factor as a reagent therein that is responsive to the anticoagulant/antithrombotic; and
a third channel without the anticoagulant/antithrombotic as a reagent therein and also without the blood factor as a reagent therein;
preparing a first plasma sample that has a clotting time that may be altered by the presence of the anticoagulant/antithrombotic but is deficient in the blood factor;
adding a first portion of the first plasma sample to the first channel of the first cartridge;
adding a second portion of the first plasma sample to the second channel of the first cartridge;
adding a third portion of the first plasma sample to the third channel of the first cartridge;
determining the time required for a clot to be formed in each of the first, second and third channels for the first plasma sample;
preparing a second plasma sample that comprises a neutralizing agent for the anticoagulant/antithrombotic;
selecting a second test cartridge having a first channel with the anticoagulant/antithrombotic as a reagent therein, a second channel with the anticoagulant/antithrombotic as a reagent therein and also with the blood factor therein, and a third channel without the anticoagulant/antithrombotic as a reagent therein and also without the blood factor as a reagent therein;
adding a first portion of the second plasma sample to the first channel;
adding a second portion of the second plasma sample to the second channel;
adding a third portion of the second plasma sample to the third channel;
determining the time required for a clot to be formed in each of the first, second and third channels for the second plasma sample, wherein the anticoagulant/antithrombotic reagent is heparin and the blood factor is antithrombin III (ATIII).

9. The method according to claim 8, wherein the first channel of the first cartridge and the first channel of the second cartridge has heparin as a reagent in the amount of between approximately 0.1–10.0 Units/ml.

10. The method of claim 8, wherein the second plasma sample includes protamine as the neutralizing agent.

11. The method of claim 8, wherein the second plasma sample includes a polycation as the neutralizing agent.

12. The method of claim 8, wherein the second plasma sample includes a quartenaryamine as the neutralizing agent.

13. The method of claim 8, wherein the second plasma sample includes hexadimethrine bromide as the neutralizing agent.

14. The method of claim 8, wherein the second plasma sample includes heparinase as the neutralizing agent.

15. The method of claim 8, wherein the second channel of the first cartridge and the second channel of the second cartridge has AT III as a reagent in the amount of between approximately 0.1–10.0 Units/ml.

16. A quality test kit comprising:
    (1) a first plasma sample that has a clotting time that may be altered by the presence of heparin but is deficient in antithrombin III (AT III);
    (2) a second plasma sample that includes an agent capable of neutralizing the heparin and
    (3) a first and second test cartridge having a first channel with heparin as a reagent therein and a second channel without heparin therein.

17. The kit of claim 16 wherein the second plasma sample includes protamine as the neutralizing agent.

18. The kit of claim 16 wherein the second plasma sample includes a polycation as the neutralizing agent.

19. The kit of claim 16 wherein the second plasma sample includes a quartenaryamine as the neutralizing agent.

20. The kit of claim 16 wherein the second plasma sample includes hexadimethrine bromide as the neutralizing agent.

21. The kit of claim 16 wherein the second plasma sample includes heparinase as the neutralizing agent.

* * * * *